US00PP31482P2

(12) United States Plant Patent
Van Swieten

(10) Patent No.: US PP31,482 P2
(45) Date of Patent: Feb. 25, 2020

(54) ***PHALAENOPSIS* ORCHID PLANT NAMED 'PHALGLAOR'**

(50) Latin Name: ***Phalaenopsis* hybrid**
Varietal Denomination: PHALGLAOR

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/501,177

(22) Filed: Mar. 1, 2019

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./263.1, 311
See application file for complete search history.

(56) References Cited

PUBLICATIONS

EU Community Plant Variety Rights Application No. 2017/2374, Application n°A201702680, filed Sep. 26, 2017, 8 pages.
EU Community Plant Variety Office Official Gazette, 6.2017, Dec. 15, 2017, cover page and pp. 38, 58.
EU Community Plant Variety Rights Certificate on the Grant, EU 50587, Nov. 5, 2018, 2 pages.
EU Community Plant Variety Office Official Gazette, 1.2019, Feb. 15, 2019, cover page and p. 86.

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new and distinct variety of *Phalaenopsis* plant named 'PHALGLAOR', particularly characterized by having reddish-purple flowers with light purple edges and centers and red-purple lips, 1 to 3 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALGLAOR'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALGLAOR'.

The new *Phalaenopsis* plant is a product of a planned breeding program conducted by the inventor in Bleiswijk, The Netherlands. The objective of this breeding program was to create a new *Phalaenopsis* plant with numerous attractive reddish-purple flowers having light purple edges and centers and red-purple lips, suitable for potted plant production.

The new *Phalaenopsis* plant 'PHALGLAOR' is a result of cross-pollination made by the inventor in March 2008 in Bleiswijk, The Netherlands, of the proprietary female, or seed parent, *Phalaenopsis* hybrid '26718-03' (unpatented) with the proprietary male, or pollen parent, *Phalaenopsis* hybrid '13522-02' (unpatented).

The new *Phalaenopsis* was selected by the inventor as a single plant within the progeny of the stated cross-pollination in a controlled greenhouse in Bleiswijk, The Netherlands, in April 2011. Asexual reproduction of the new *Phalaenopsis* plant by meristem tissue culture since 2014 in Bleiswijk, The Netherlands, has demonstrated that the new variety reproduces true to type with all of the characteristics, as herein described, firmly fixed and retained through successive generations.

Plant Breeder's Rights for this variety have been applied for in Europe on Sep. 26, 2017, by Applicant who obtained the subject matter disclosed directly from the Inventor. 'PHALGLAOR' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, The Netherlands, and can be used to distinguish 'PHALGLAOR' as a new and distinct variety of *Phalaenopsis* plant:

1) Reddish-purple flowers with light purple edges and centers and red-purple lips (the area of light purple edge increases during flower development);
2) 1 to 3 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, The Netherlands, from 50-week-old plants in January 2019. Colors in the photographs may differ from the color values cited in the detailed botanical description, which accurately describe the actual colors of the new variety.

DESCRIPTION OF THE NEW VARIETY

Figure 1:
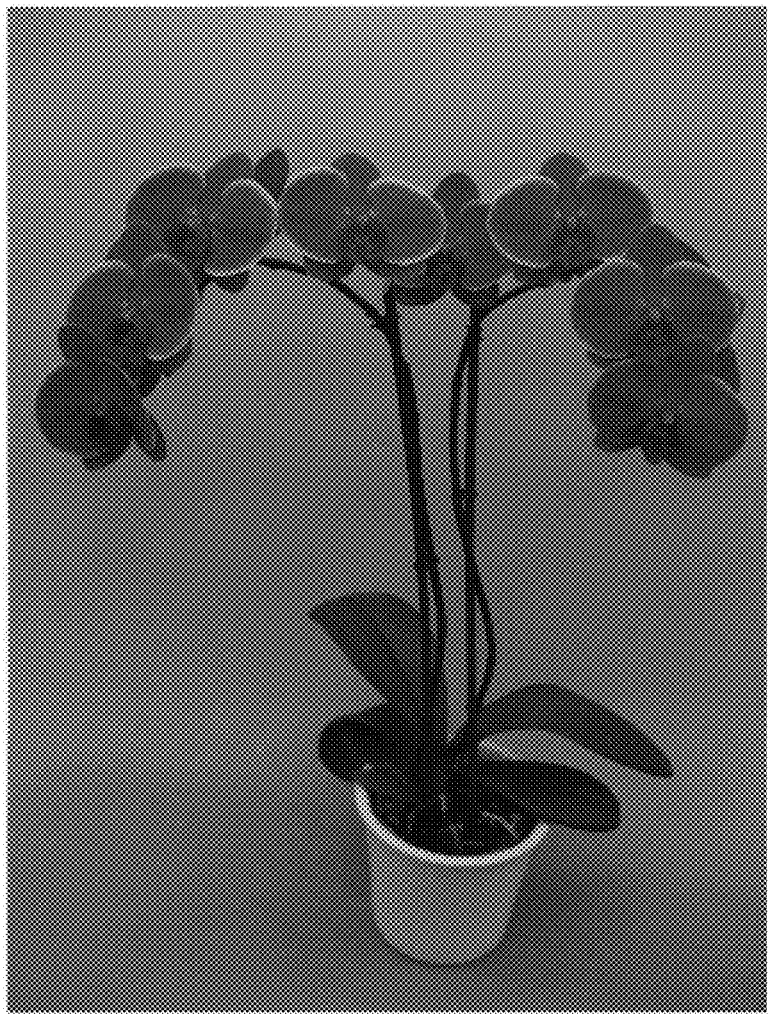
FIG. 1 shows the overall plant habit, including blooms and foliage of 'PHALGLAOR'.
Figure 2:
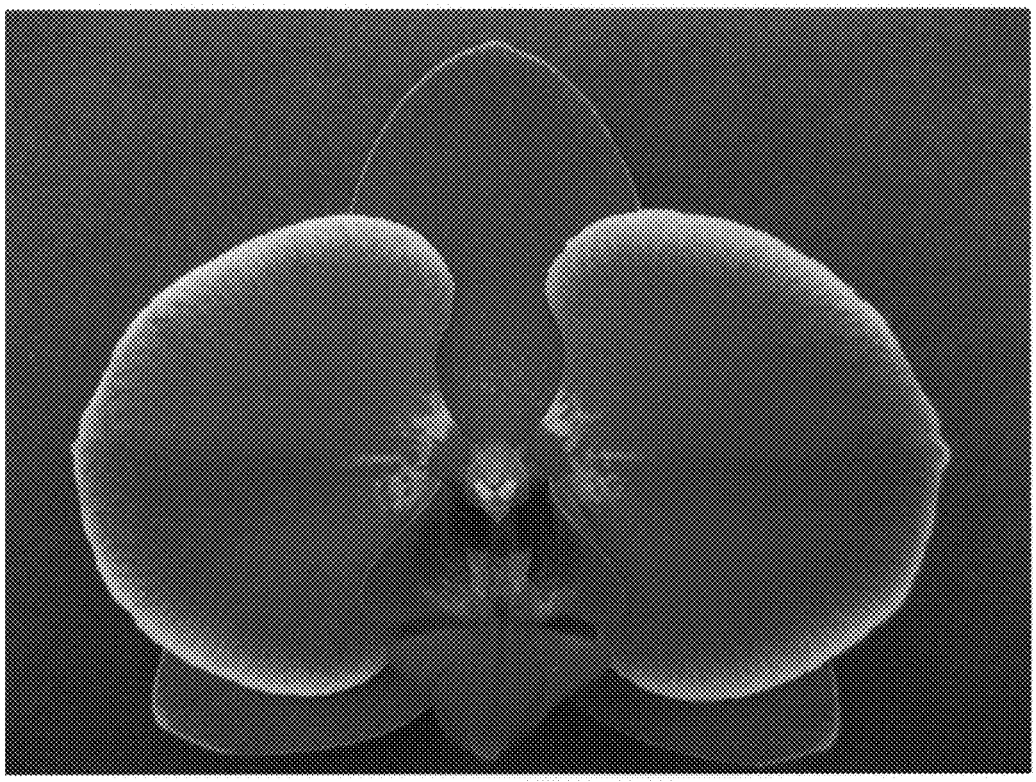
FIG. 2 shows a close-up of a flower of 'PHALGLAOR'.
Figure 3:
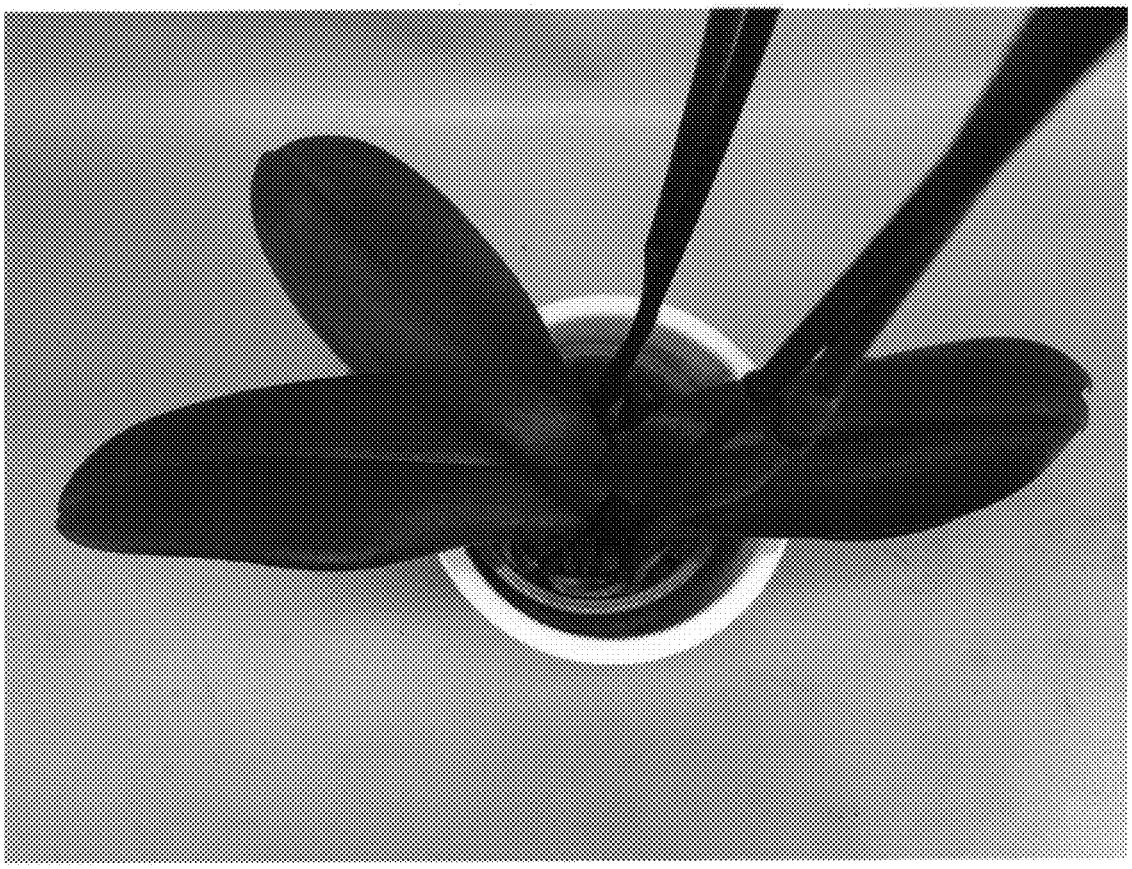
FIG. 3 shows an overhead view of the leaves of 'PHALGLAOR'.

The following detailed description sets forth the distinctive characteristics of 'PHALGLAOR'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, The Netherlands. Observations and measurements were made in January 2019 on flowering plants which were planted in 12-centimeter (diameter) pots. After in-vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALGLAOR'.

Parentage:

*Female parent*.—*Phalaenopsis* cultivar '26718-03' (unpatented).

*Male parent*.—*Phalaenopsis* cultivar '13522-02' (unpatented).

Propagation:

*Type*.—Meristem tissue culture.

Roots:

*Root description*.—Greyed-green (between RHS 190B and 190C) colored roots with branching lateral roots having green (RHS 146C) colored root tips with a touch of dark red (RHS 187B).

Plant:

*Commercial crop time to flowering*.—Following asexual propagation (in-vitro), the rooted cuttings grow for 20-24 weeks. After transplantation into 12-cm pots, the plants are finished after 48 to 50 weeks.

*Growth habit of peduncle*.—Upright to slightly pendant with raceme inflorescence.

*Height (from soil level to top of inflorescence)*.—Approximately 59.0 cm to 64.0 cm.

*Width (measured from leaf tips)*.—About 31.0 cm to 34.0 cm.

*Vigor*.—Moderate.

Leaves:

*Mature leaves*.—Quantity per plant: 8 to 10 leaves are produced before flowering. Length (fully expanded): 19.0 cm to 21.0 cm. Width: 7.0 cm to 8.0 cm. Shape: Oblong. Base shape: Moderately elongated. Apex: Obtuse to acute unequal. Leaf blade angle with the petiole (measured from the horizontal position): Between 25 degrees and 40 degrees. Leaf margin: Entire. Color: Upper surface: RHS 147A. Lower surface: RHS 146B with dark red tint (RHS 187A) around edge. Texture (upper surface): Rough. Texture (lower surface): Smooth. Thickness: 2.4 mm to 2.9 mm. Venation: Pattern: Parallel. Color of the midvein: Upper surface: RHS 147A. Lower surface: RHS 146B.

Peduncle:

*Quantity per plant*.—1 to 3.

*Number of flowers per peduncle*.—8 to 12.

*Length*.—59.0 cm to 64.0 cm.

*Diameter*.—5.9 mm to 6.4 mm.

*Strength*.—Strong.

*Aspect*.—Upright to slightly pendant.

*Texture*.—Smooth.

*Color*.—Mix of brown (RHS 200B) and light green (RHS 195A).

*Internode length*.—3.5 cm to 4.5 cm.

Inflorescence description:

*Appearance*.—Upright to slightly pendant, raceme inflorescence with bilaterally symmetrical flowers that open in succession beginning with the lowermost flower.

*Inflorescence size*.—Height (from base to tip): 200.0 mm to 250.0 mm. Diameter: 120.0 mm to 150.0 mm.

*Flowering time*.—First flowers can be expected 10 to 11 months after planting in a 12-cm pot.

*Flower*.—Height: 70.0 mm to 75.0 mm. Diameter: 85.0 mm to 90.0 mm. Depth of lip: 21.0 mm to 23.0 mm.

*Flower longevity*.—On the plant: 9 to 14 weeks.

*Fragrance*.—Absent.

*Flower bud*.—Average size: Large. Length: 24.0 mm to 26.0 mm. Width: 20.0 mm to 22.0 mm. Shape: Egg shaped. Color: Purplish-red (RHS N77B).

*Petals*.—Arrangement: Open/free. Shape: Semi-circular. Apex: Rounded to slightly mucronated asymmetric. Margin: Entire. Length (from base to tip): 37.0 mm to 39.0 mm. Width: 47.0 mm to 49.0 mm. Color (when fully opened): Upper surface: Basic color: Reddish-purple (RHS N78A). Over color: Small light reddish-purple center and edge (RHS N78C). Lower surface: Basic color: Reddish-purple (RHS N78B). Over color: Light purple (RHS 76A).

*Dorsal sepal*.—Shape: Elliptic. Apex: Obtuse symmetric. Margin: Entire. Length (from base to tip): 40.0 mm to 42.0 mm. Width: 31.0 mm to 33.0 mm. Color (when fully opened): Upper surface: Basic color: Mix of dark purplish-red (RHS N79C) and reddish-purple (RHS N78A). Over color: Very small light yellow-green (RHS 195C). Lower surface: Basic color: Reddish-purple (RHS N78B). Over color: Yellow-green (RHS 195B) in the middle.

*Lateral sepals*.—Shape: Ovate. Apex: Obtuse asymmetric. Margin: Entire. Length (from base to tip): 41.0 mm to 43.0 mm. Width: 28.0 mm to 30.0 mm. Color (when fully opened): Upper surface: Basic color: Mix of dark purplish-red (RHS N79C) and reddish-purple (RHS N78A). Over color: Slightly light yellow-green (RHS 195B) at the base; spotted (RHS 187B). Lower surface: Basic color: Reddish-purple (RHS N78B). Over color: Purplish-red (RHS N77B) with a touch of light yellow-green (RHS 195C).

*Labellum* (*lip*).—Whiskers: Present. Length of whiskers: 16.0 mm to 18.0 mm. Color of whiskers: Dark red (RHS 187B). Pubescence on the lip: Absent.

*Lateral lobe*.—Shape: Type V (as described in the International Union for the Protection of New Varieties of Plants (UPOV) Test Guidelines for *Phalaenopsis*); spatulate. Margin: Slightly wavy. Length: 18.0 mm to 20.0 mm. Width: 14.0 mm to 16.0 mm. Color: Upper surface: Very light purple (RHS 76C) at the base; dark red (RHS 187B) on one side and dark purplish-red (RHS N79C) toward the other side. Lower surface: Light purplish-grey (RHS N187D) at the base toward one side; dark purplish-red (RHS N79C) and dark red (RHS 187B) toward margin on the other side.

*Apical lobe*.—Shape: Triangular. Margin: Entire. Length: 20.0 mm to 22.0 mm. Width: 23.0 mm to 25.0 mm. Color: Upper surface: Dark purplish-red (RHS N79C) at the base and dark red (RHS 187B) toward whiskers. Lower surface: Purple-red (mix of RHS N77B and N78B) at the base and in the middle; dark purplish-red (RHS N79C) toward margins; dark red wings (RHS 187B) toward the tip.

*Callus*.—Average size: Medium to large. Height: 7.0 mm to 8.0 mm. Length: 5.0 mm to 6.0 mm. Width: 4.0 mm to 5.0 mm. Color: White (RHS N155B) at the base and light yellow (RHS 11C) toward the top; dotted (RHS N79C).

Reproductive organs:

*Column*.—Length: 8.0 mm to 10.0 mm. Diameter: 5.5 mm to 6.0 mm. Color: Reddish-purple (RHS N78B) on sides and in the middle (RHS N78A).

*Pollinia*.—Quantity: 2. Diameter: 1.0 mm to 1.2 mm. Color: Orange (RHS 24A).

*Ovary*.—Length: 10.0 mm to 12.0 mm. Diameter: 2.1 mm to 2.3 mm. Color: Yellow-green (RHS 195B) and light reddish-purple (RHS N78D) toward the flower.

*Pedicel*.—Length: 33.0 mm to 35.0 mm. Diameter: 2.5 mm to 2.8 mm. Color: Yellow-green (RHS 146A) and slightly dark red (RHS 187A) at the base; yellow-green (RHS 195B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALGLAOR' differs from female parent plant '26718-03' (unpatented) in that 'PHALGLAOR' has obtuse dorsal sepal apexes, whereas '26718-03' has emarginated dorsal sepal apexes. Additionally, 'PHALGLAOR' has longer whiskers and longer dorsal sepals than '26718-03'.

'PHALGLAOR' differs from male parent plant '13522-02' (unpatented) in that 'PHALGLAOR' has obtuse dorsal sepal apexes, whereas '13522-02' has rounded dorsal sepal apexes. Additionally, 'PHALGLAOR' has shorter whiskers than '13522-02'.

'PHALGLAOR' is most similar to the commercial *Phalaenopsis* plants named 'PHALUFREL' (U.S. Plant Pat. No. 29,259) and 'PHALFAREN' (U.S. Plant Pat. No. 29,999). 'PHALGLAOR' differs from the commercial variety 'PHALUFREL' in that 'PHALGLAOR' has obtuse to acute unequal leaf apexes and dark red whiskers (RHS 187B), whereas 'PHALUFREL' has rounded unequal leaf apexes and dark red (RHS 187A) whiskers with white tips. Additionally, 'PHALGLAOR' has longer whiskers and shorter dorsal sepals than 'PHALUFREL'.

'PHALGLAOR' differs from the commercial variety 'PHALFAREN' in that 'PHALGLAOR' has dark red whiskers (RHS 187B), whereas 'PHALFAREN' has whiskers that are a mix of dark purplish-red (RHS N79A) and dark red (RHS 187A). Additionally, 'PHALGLAOR' has longer whiskers and wider apical lobes than 'PHALFAREN'.

I claim:

1. A new and distinct variety of *Phalaenopsis* plant named 'PHALGLAOR', substantially as described and illustrated herein.

* * * * *